(12) United States Patent
Roby

(10) Patent No.: US 6,894,140 B2
(45) Date of Patent: May 17, 2005

(54) FAST CURING COMPOSITIONS

(75) Inventor: Mark Roby, Killingworth, CT (US)

(73) Assignee: Tyco Healthecare Gropu LP, Norwalk, CT (US)

(*) Notice: Subject to any disclaimer, the term of this patent is extended or adjusted under 35 U.S.C. 154(b) by 0 days.

(21) Appl. No.: 10/694,499

(22) Filed: Oct. 27, 2003

(65) Prior Publication Data

US 2004/0115229 A1 Jun. 17, 2004

Related U.S. Application Data

(60) Provisional application No. 60/421,940, filed on Oct. 28, 2002.

(51) Int. Cl.[7] ............................................. C08G 18/77
(52) U.S. Cl. ....................... 528/70; 528/904; 523/118; 514/479; 606/214
(58) Field of Search .................. 528/70, 904; 523/118; 514/479; 606/214

(56) References Cited

U.S. PATENT DOCUMENTS

| | | | |
|---|---|---|---|
| 3,463,762 A | * | 8/1969 | Trischler .................... 525/453 |
| 4,623,709 A | | 11/1986 | Bauriedel |
| 4,740,534 A | * | 4/1988 | Matsuda et al. ............ 523/111 |
| 4,826,945 A | | 5/1989 | Cohn et al. |
| 4,829,099 A | | 5/1989 | Fuller et al. |
| 4,994,542 A | * | 2/1991 | Matsuda et al. .............. 528/70 |
| 5,166,300 A | | 11/1992 | Rumon et al. |
| 5,266,608 A | | 11/1993 | Katz et al. |
| 5,296,518 A | | 3/1994 | Grasel et al. |
| 6,423,810 B1 | | 7/2002 | Huang et al. |
| 6,566,406 B1 | | 5/2003 | Pathak et al. |
| 2003/0012734 A1 | | 1/2003 | Pathak et al. |
| 2003/0108511 A1 | | 6/2003 | Sawhney |
| 2004/0023842 A1 | | 2/2004 | Pathak et al. |

* cited by examiner

*Primary Examiner*—Rachel Gorr

(57) ABSTRACT

Fast curing surgical adhesives and sealants contain an NCO-terminated hydrophilic urethane prepolymer derived from an aromatic diisocyanate and a polyol. Substantially all the aromatic diisocyanate used to prepare the NCO-terminated hydrophilic urethane prepolymer is in the para form. Optionally, the aromatic diisocyanate is substituted with at least one electron withdrawing group, such as, for example, a fluorine group.

25 Claims, No Drawings

FAST CURING COMPOSITIONS

This application claims priority from Provisional Application Ser. No. 60/421,940 filed on Oct. 28, 2002.

BACKGROUND

1. Technical Field

The present disclosure relates to surgical adhesives and sealants. More specifically, this disclosure relates to fast curing biocompatible compositions based on aromatic diisocyanates.

2. Description of the Related Art

In recent years there has developed increased interest in replacing or augmenting sutures with adhesive bonds. The reasons for this increased interest include: (1) the potential speed with which repair might be accomplished; (2) the ability of a bonding substance to effect complete closure, thus preventing seepage of fluids; and (3) the possibility of forming a bond without excessive deformation of tissue.

Studies in this area, however, have revealed that, in order for surgical adhesives to be accepted by surgeons, they must possess a number of properties. First, they must exhibit high initial tack and an ability to bond rapidly to living tissue. Secondly, the strength of the bond should be sufficiently high to cause tissue failure before bond failure. Thirdly, the adhesive should form a bridge, preferably a permeable flexible bridge. Fourthly, the adhesive bridge and/or its metabolic products should not cause local histotoxic or carcinogenic effects.

A number of adhesive systems such as alkyl cyanoacrylates, polyacrylates, maleic anhydride/methyl vinyl ethers, epoxy systems, polyvinyl alcohols, formaldehyde and gluteraldehyde resins and isocyanates have been investigated as possible surgical adhesives. None has gained acceptance because each fails to meet one or more of the criteria noted above. The principal criticism of these systems has been the potential toxicity problems they pose.

Isocyanate-based adhesive/sealant compositions are disclosed, for example, in U.S. Pat. Nos. 5,173,301; 4,994,542; and 4,740,534, the disclosures of which are incorporated herein in their entirety by this reference.

It would be desirable to provide novel metabolically-acceptable bioabsorbable diisocyanate-based adhesives and in particular metabolically-acceptable surgical adhesives. It would also be desirable to provide metabolically-acceptable surgical adhesives which are biodegradable. It would also be desirable to provide a method for closing wounds in living tissue by use of novel, metabolically-acceptable surgical adhesives which are low in toxicity as a consequence of their physical properties.

SUMMARY

The present surgical adhesive and sealant compositions contain an NCO-terminated hydrophilic urethane prepolymer derived from an aromatic diisocyanate and a hydrophilic polyether polyol. Substantially all the aromatic diisocyanate used to prepare the NCO-terminated hydrophilic urethane prepolymer is in the para form. Optionally, the aromatic diisocyanate is substituted with at least one electron withdrawing group.

DETAILED DESCRIPTION OF PREFERRED EMBODIMENTS

The NCO-terminated hydrophilic urethane prepolymer used in the present compositions are derived from (a) at least one aromatic diisocyanate and (b) at least one hydrophilic polyether polyol.

Suitable examples of aromatic polyisocyanates are those containing 6 to 20 carbon atoms, not including the carbon atoms in the NCO groups. Substantially all the aromatic diisocyanate employed is in the para configuration. By the term "substantially all" it is meant that at least 80 mole percent of the diisocyanate is the para form. Preferably 95 mole percent of the aromatic diisocyanate employed is in the para configuration. Suitable aromatic diisocyanates include, but are not limited to, p-phenylene diisocyanate (hereinafter referred to as PDI), 2,4-tolylene diisocyanate (TDI), diphenylmethane-2,4'-diisocyanate (MDI), p isocyanatophenyl sulfonyl isocyanate, and the like.

Optionally, the aromatic diisocyanate is substituted with one or more electron-withdrawing groups. Suitable electron-withdrawing groups include halogen (such as, for example, fluorine or chlorine), carbonyl, carboxyl, nitrile, nitro, phosphonate or phosphate ester groups. The diisocyanate can be substituted with anywhere from 1 to 4 electron withdrawing groups. Fluorine is a particularly useful electron withdrawing group, especially when the diisocyanate is fully substituted (i.e., with four fluorine groups). F-containing polyisocyanates can be produced according to the methods described in J. Macromol. Sci.-Phys., BI, 831 (1967) and Japanese Laid-Open Pat. No. 108055/1982, the disclosure of which is incorporated herein by reference.

Illustrative of suitable hydrophilic polyether polyols (b) are the reaction product of ethylene oxide or combinations of ethylene oxide with other alkylene oxide(s) with one or more compounds containing at least two active hydrogen atoms, such as polyhydric alcohols, polyhydric phenols, amines, polycarboxylic acids, phosphorous acids and the like. Suitable examples of polyhydric alcohols include dihydric alcohols, such as ethylene glycol, propylene glycol, 1,3- and 1,4-butanediols, 1,6-hexanediol, nehtylene oxidepentyl glycol, diethylene glycol, bis(hydroxymethyl)cyclohexane, bis(hydroxyethyl)benzene, hydrogenated bisphenol A, hydrogenated bisphenol F, polytetramethylene glycols, polyester diols and silanol-terminated polysiloxanes; trihydric alcohols, such as glycerol, trimethylol propane, trimethylol ethane, 1,2,3-butane triol, 1,2,6-hexane triol and polyester triols; and polyhydric alcohols having 4 to 8 or more hydroxyl groups, such as pentaerythritol, diglycerol, .alpha.-methylglucoside, sorbitol, xylitol, mannitol, glucose, fructose, sucrose, and the like. Exemplary of suitable polyhydric phenols are mono- and polynuclear phenols, such as hydroquinone, catechol, resorcin, pyrogallol, and bisphenols (bisphenol A, bisphenol F, bisphenol S, and the like), as well as phenol-formaldehyde condensation products. Suitable amines include ammonia; alkanol amines, such as mono-, di- and tri-ethanol amines, isopropanol amines and the like; aliphatic, aromatic, araliphatic and alicyclic monoamines, such as $C_1$ to $C_{20}$ alkyl amines (methyl-, ethyl-, isopropyl-, butyl-, octyl-, and laurylamines, and the like), aniline, toluidine, naphthylamines, benzylamine, cyclohexylamine and the like, aliphatic, aromatic, alicyclic and araliphatic polyamines, such as $C_2$ to $C_6$ alkylene diamines (such as ethylene diamines), diethylene triamine, tolylene diamines, phenylene diamines, xylylene diamines, methylene dianilines, diphenylether diamines, isophorone diamine, cyclohexylene diamines, dicyclohexylmethane diamines and the like; and heterocyclic polyamines, such as piperazine, N-aminoethyl-piperazine, and other heterocyclic polyamines.

Suitable alkylene oxide, which may be employed in combination with ehtylene oxide for producing polyether polyols, include, for example, propylene oxide, 1,2-, 2,3-, 1,3-, and 1,4-butylene oxides, styrene oxide, epichlorohydrin and the like, as well as combinations of two or more of them.

The addition of ehtylene oxide or the combination thereof with alkylene oxide to the active hydrogen atom-containing compounds can be carried out in any conventional manner, with or without catalysts, such as alkaline catalysts, amine catalysts, or acidic catalysts, under normal or elevated pressure, in a single step or in a multi-stage process. The addition of ehtylene oxide and alkylene oxide may be performed by random-addition, block-addition or a combination thereof, for example random-addition followed by block-addition. Random-addition is preferred.

The hydrophilic polyether polyols can advantageously have an equivalent weight (molecular weight per hydroxyl group) of 100 to 5,000 daltons, preferably 200 to 3,000 daltons, and an oxyethylene content of at least 30%, preferably 50–90% by weight. Polyether polyols having an equivalent weight higher than 5,000 may result in compositions having relatively high viscosities which may be useful for some, but not all surgical adhesive applications, while an equivalent weight of less than 100 results in compositions having relatively low flexibility which may be useful for some, but not all surgical adhesive applications. Polyether polyols of oxyethylene content less than 30% by weight, having insufficient hydrophilic nature, may have a poor reactivity with body fluids possibly resulting in a reduced cure rate and poor bonding power with water-rich tissue. The content of the primary hydroxyl groups of the polyether polyols can advantageously be at least 30%, more preferably at least 50%, most preferably at least 70%.

The whole polyols (b) used for producing the NCO-terminated urethane prepolymer, have an oxyethylene content suitably of at least 30%, preferably 50–90% by weight, an average equivalent weight of suitably 100–5,000 daltons, preferably 200–3,000 daltons, and suitably 2 to 8 hydroxyl groups (average), preferably 2 to 4 hydroxyl groups.

In reacting the aromatic polyisocyanate (a) with at least one hydrophilic polyether polyol (b) to form NCO-terminated hydrophlic urethane prepolymers, the ratio of NCO/OH is generally 1.5 to 5.0, preferably 1.7 to 3.0. The reaction of (a) with (b) to form the prepolymer can be performed in any conventional manner. The reaction may be carried out in the presence of a catalyst.

The NCO-content of the present NCO-terminated hydrophilic prepolymers is suitably 1 to 10%, preferably 2 to 8% by weight.

The present adhesive or sealant compositions may contain, if desired, physiologically active materials, such as antimicrobials, local anesthetics, antihistamines, antiphlogosis analgestics, antibiotics, astringents, vitamins, antifungal agents, peripheral nervous system anesthetics, vasodilators, hormones, crude drug essences, tinctures, crude drug powders, hypotensive agents, and the like; fillers, for example, carbon black, metal oxides, such as red iron oxide and titanium dioxide, silicates, such as calcium silicates and sodium silicates, acrylic resin powders, various ceramic powders, and the like; softening agents, such as DBP (dibutylphosphate), DOP (dioctylphosphate), TCP (tricresylphosphate), tributoxyethylphosphates, and other esters of various types; and stabilizers, such as trimethyldihydroquinone, phenyl-β-naphthyl amine, p-isopropoxydiphenylamine, diphenyl-p-phenylene diamine, and the like. These additives may be used in amounts of up to 20%, preferably up to 5%, based on the weight of the composition.

The NCO-terminated prepolymer is rapidly polymerized in the presence of trace amounts of water, such as moisture in the air, resulting in the formation of a tough membrane. Accordingly, it is preferable to use dry materials as these main components and any other compounding additives, and it is preferred to exclude moisture during the production of the adhesives. Adhesives, thus-obtained, can be stored for a long period of time within airtight vessels, such as an ampule.

In applying the adhesives of the present disclosure in surgery, suitable application methods include those employing brushes, tweezers, applicators, specially-designed spatula or syringes, or the like; and those involving spray coating using inert gases, such as nitrogen or the like. Bonding of tissues can be achieved, for example, by direct coating techniques, simply applying the adhesive to the tissues; by cover-coating techniques, using, as an aid for hemostasis or anastomosis, thin sheets or meshes made of polyesters (such as Dacron), oxidized cellulose, collagen, polyurethanes or the like, cotton like materials, or fragments of tissues, such as veins, musculation or mascular membrane or the like (wherein these materials are applied onto the affected parts followed by coating with the adhesives); or by sealing techniques for sutured parts, wherein sutures are partly applied followed by applying the adhesive to seal the remaining conjugation parts. The adhesives can be used, not only for tissue adhesion, but also as coating, embolus or sealing materials in cardiovascular surgery via direct coating or injection by catheters. Applicable tissues include, for example, vascular vessels, heart, lung, esophagus, stomach, liver, pancreas, spleen, skin, and the like.

The surgical adhesives according to the present disclosure, comprising NCO-terminated hydrophilic urethane prepolymer derived from an aromatic diisocyanate and hydrophilic polyether polyol, have a sufficiently high cure rate and provide sufficient bonding power for tissues, even without any catalyst.

In addition, the adhesives of the present disclosure can provide sufficient cure rate, bonding power to tissue, and flexibility to permit body movement, required for surgical adhesives, without using any organic solvents.

Accordingly, application of the adhesives of the present disclosure to surgical operations makes it possible to perform operations with the method of adhesion, instead of suturing as in a conventional operation. Thus, there can be attained remarkable improvements in medical technology, such as shortening of operation time, hemostasis, prevention of enzymes leaking from viscera or the like, prevention of minute blood vessel occlusion, and nerve anastomosis, as well as provisional fixing before suturing, and ensuring of bonding by the combination of adhesion with suturing. Furthermore, the present compositions can provide high reliability and high efficiency, not only in an operation, but also in medical treatments at large, for example, joining of incised wound or cutting portions, adhesive treatment in dental surgery, curative means by controlled release of drugs in combination with physiologically active materials, and so on.

It will be understood that various modifications may be made to the embodiment disclosed herein. Therefore the above description should not be construed as limiting, but merely as exemplifications of preferred embodiments. Those skilled in the art will envision other modifications within the scope and spirit of the claims appended hereto.

I claim:

1. A tissue adhesive composition comprising at least one sterilized NCO-terminated hydrophilic urethane prepolymer derived from (a) an aromatic diisocyanate substantially all of which is in the para configuration substituted with at least one electron withdrawing group and (b) a polyol component.

2. A tissue adhesive composition comprising at least one sterilized NCO-terminated hydrophilic urethane prepolymer derived from (a) an aromatic diisocyanate substantially all of which is in the para configuration substituted with at least one fluorine group and (b) a polyol component comprising ethylene oxide.

3. The adhesive of claim 1, wherein said aromatic diisocyanate substituted with at least one electron withdrawing group is selected from the group consisting of p-phenylene diisocyanate and p isocyanatophenyl sulfonyl isocyanate.

4. The adhesive of claim 1, wherein said aromatic diisocyanate is substituted with at least two electron withdrawing groups.

5. The adhesive of claim 1, wherein said aromatic diisocyanate is substituted with four electron withdrawing groups.

6. The adhesive of claim 1, wherein said electron withdrawing group is selected from the group consisting of halogen groups, carbonyl groups, carboxyl groups, nitrite groups, nitro groups, phosphonate groups, phosphate ester groups and combinations thereof.

7. The adhesive of claim 1, wherein said electron withdrawing group is a fluorine group.

8. The adhesive of claim 1, wherein said aromatic diisocyanate is substituted with four fluorine groups.

9. The adhesive of claim 1, wherein said polyol component is selected from the group consisting of polyether polyols.

10. The adhesive of claim 1, wherein said polyol component is the reaction product of one or more alkylene oxides with one or more compounds containing at least two active hydrogen atoms.

11. The adhesive of claim 1, wherein said polyol component is the reaction product of ethylene oxides with one or more compounds containing at least two active hydrogen atoms.

12. The adhesive of claim 1, wherein said polyol component is the reaction product of one or more alkylene oxides with one or more compounds selected from the group consisting of polyhydric alcohols, polyhydric phenols, amines, polycarboxylic acids and phosphorous acids.

13. The adhesive of claim 1, wherein said polyol component is the reaction product of one or more alkylene oxides selected from the group consisting of ethylene oxide, propylene oxide, 1,2-butylene oxide, 2,3-butylene oxide, 1,3-butylene oxide, 1,4-butylene oxide, styrene oxide and epichlorohydrin with one or more compounds containing at least two active hydrogen atoms.

14. The adhesive of claim 1, wherein said polyol component is selected from the group consisting of polyether polyols having an equivalent weight of 100 to 5,000 daltons.

15. The adhesive of claim 1, wherein said polyol component is selected from the group consisting of polyether polyols having an oxyethylene content of suitably at least 30%.

16. The adhesive of claim 1, further comprising one or more physiologically active materials selected from the group consisting of antimicrobials, local anesthetics, antihistamines, antiphlogosis analgestics, antibiotics, astringents, vitamins, antifungal agents, peripheral nervous system anesthetics, vasodilators, hormones, crude drug essences, tinctures, crude drug powders and hypotensive agents.

17. The adhesive of claim 1, further comprising one ore more fillers selected from the group consisting of carbon black, metal oxides, silicates, acrylic resin powders and ceramic powders.

18. The adhesive of claim 1, further comprising one ore more softening agents selected from the group consisting of dibutylphosphate, dioctylphosphate, tricresylphosphate and tributoxyethylphosphates.

19. The adhesive of claim 1, further comprising one ore more stabilizers selected from the group consisting of trimethyldihydroquinone, phenyl-.beta.-naphthyl amine, p-isopropoxydiphenylamine and diphenyl-p-phenylene diamine.

20. A method comprising: applying an adhesive composition comprising at least one sterile NCO-terminated hydrophilic urethane prepolymer derived from (a) an aromatic diisocyanate substantially all of which is in the para configuration substituted with at least one electron withdrawing group and (b) a polyol component to tissue.

21. A method as in claim 20 wherein the step of applying an adhesive composition comprises applying the adhesive composition over a tissue defect.

22. A method as in claim 20 wherein the step of applying an adhesive composition comprises applying the adhesive composition to seal a defect in an anatomical vessel.

23. A method as in claim 20 wherein the step of applying an adhesive composition comprises applying the adhesive composition over a defect in lung tissue.

24. A method as in claim 20 wherein the step of applying an adhesive composition comprises approximating two tissue surfaces and applying the adhesive composition in contact with the approximated tissue surfaces.

25. A method of preparing a tissue adhesive comprising reacting (a) an aromatic diisocyanate substantially all of which is in the para configuration and substituted with at least one electron withdrawing group with (b) a polyol component to a form a prepolymer; and sterilizing the resulting product.

* * * * *